United States Patent [19]

Fürst et al.

[11] 3,965,128
[45] June 22, 1976

[54] 6β,7β-EPOXY-1α,2α-METHYLEN-D-HOMO-4-PREGNEN-3,20-DIONES

[75] Inventors: Andor Fürst, Basel; Marcel Müller, Frenkendorf; Leo Alig, Liestal; Peter Keller, Therwil, all of Switzerland; Ulrich Kerb; Rudolf Wiechert, both of Berlin, Germany

[73] Assignee: Hoffmann-La Roche Inc., Nutley, N.J.

[22] Filed: Sept. 23, 1974

[21] Appl. No.: 508,492

[30] Foreign Application Priority Data
Sept. 26, 1973 Germany............................ 2349024

[52] U.S. Cl.............................. 260/348 C; 260/999; 260/468.5
[51] Int. Cl.²..................................... C07D 303/44
[58] Field of Search................................ 260/348 C

*Primary Examiner*—Norma S. Milestone
*Attorney, Agent, or Firm*—Samuel L. Welt; George M. Gould

[57] ABSTRACT

New 6β,7β-epoxy-17α-hydroxy or acyloxy-1α,2α-methylen-D-homo-4-pregnen-3,20-diones having surprising progestational activity are disclosed.

4 Claims, No Drawings

6β,7β-EPOXY-1α,2α-METHYLEN-D-HOMO-4-PREGNEN-3,20-DIONES

DESCRIPTION OF THE INVENTION

The present invention relates to new compounds of the formula

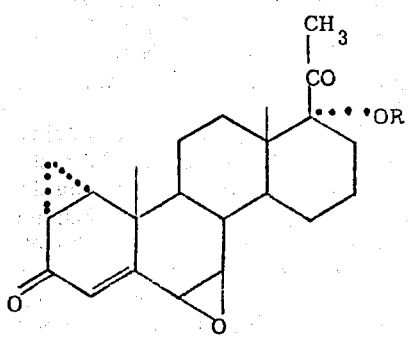

(I)

wherein R is hydrogen or acyl.

The term "acyl" as used herein is meant to include those acid radicals which are commonly employed in steroid chemistry to esterify hydroxy groups. Suitable acids for use as such esterifying agents include organic carboxylic acids having 1–15 carbon atoms. Such carboxylic acids may be unsaturated, branched chain, polybasic or may be substituted in a known manner with substituents such as hydroxy, amino, oxo or halogen. Additionally, such carboxylic acids may be cycloaliphatic, mono- or bi- cyclic aromatic, mixed aromatic-aliphatic or heterocyclic acids which, if desired, can be substituted such as by halogen in a manner known per se. Examples of preferred acids include acetic acid, propionic acid, caproic acid, enanthic acid, undecylic acid, oleic acid, trimethyl acetic acid, halo-acetic acid, dichloroacetic acid, cyclopentylpropionic acid, cyclohexylacetic acid, phenylpropionic acid, phenylacetic acid, phenoxyacetic acid, dialkylaminoacetic acid, piperidinoacetic acid, succinic acid, benzoic acid and the like. If a water soluble compound is desired then it is possible to prepare other esters using inorganic acids, such as for example sulfuric or phosphoric acid.

The new 6β,7β-epoxy, 1α,2α-methylene steroids of the present invention exhibit interesting pharmacological properties. They show a surprising progestational activity and thus the active compounds of the invention may be employed to treat gynecological disorders utilizing generally, a daily dosage of between about 1 and 100 mg. The preparation of medicinal specialty forms with the instant active compounds can be accomplished in known manner by compounding with specific additives, carrier materials and taste modifiers conventionally employed in commercial practice.

The compounds of formula I of the present invention can be prepared conveniently by treating a compound of the formula

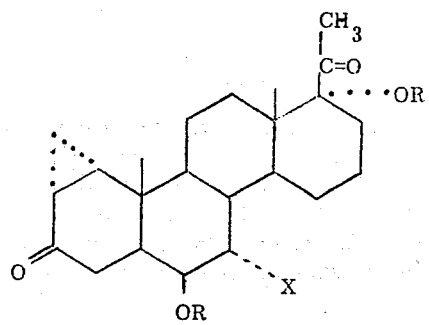

II wherein R is as above and X is chloro or bromo with base in the presence of an inert solvent. If desired a free hydroxy group can be esterified in known manner.

Suitable inert solvents include water miscible solvents, solvents such as methanol, ethanol, acetone, tetrahydrofuran, dimethylsulfoxide, as well as mixtures of these solvents such as ethanol with acetone.

The closing of the oxirane ring proceeds in a manner known per se. Suitable bases for this purpose include alkali metal carbonates and bicarbonates such as potassium carbonate and sodium bicarbonate, alkali metal hydroxides, such as potassium and sodium hydroxide, alkali metal alcoholate, such as potassium and sodium hydroxide, alkali metal alcoholate, such as potassium-tert.-butylate and the like.

Depending on the strength of the selected base and the level of the reaction temperature there is a resultant effect on the extent of saponification in the reaction product. Thus by selecting specific conditions for the reaction it is possible to obtain a free or an esterified 17-hydroxy compound. Utilizing potassium carbonate in ethanol and acetone at room temperature one obtains the 6β,7β-epoxide with the 17α-acyloxy group retained. With the same reactants but employing heat and a reaction time of 20 hours one obtains the epoxide with the 17α-acyloxy group being substantially saponified. When potassium hydroxide as base but using a shorter reaction time at room temperature one obtains the 6β,7β-epoxide with a free 17α-hydroxy group.

Re-esterification, if desired, can be carried out using a reactive acid derivative in the presence of a basic reagent. Preferred acid derivatives for this purpose include the acid anhydrides and most preferably in the presence of pyridine and at elevated temperatures.

The starting materials used in the instant process where not specifically disclosed in the literature can be prepared in analogy to known procedures. Thus the 6β-hydroxy- and the 6β-acyloxy-7α-halo-steroid, respectively, can be prepared from the corresponding Δ⁶-D-homosteroids in the manner described for the preparation of 6-OR-7-X-analogs in U.S. Pat. No. 3,496,273.

In this manner one obtains from 17a-acyloxy-1α,2α-methylene-D-homo-4,6-pregnadien-3,20-dione using N-bromo- or preferably N-chlorosuccinimide and water in the presence of perchloric acid in dioxane the following 6β-hydroxy-7α-halosteroids:

7α-bromo-6β-hydroxy-17a-acetoxy-1α,2α-methylene-D-homo-4-pregnen-3,20-dione, UV: $\epsilon_{230} = 11,500$ 7α-bromo-6β-hydroxy-17a-hexanoyloxy-1α,2α-methylene-D-homo-4-pregnen-3,20-dione as an oil, UV: $\epsilon_{230} = 11,200$ 7α-chloro-6β-hydroxy-17a-acetoxy-1α,2α-methylene-D-homo-4-pregnen-3,20-dione, UV: $\epsilon_{231} = 1300$.

From 17a-acetoxy-1α,2αmethylene-D-homo-4,6-pregnadien-3,20-dione and utilizing N-bromo- or preferably N-chlorosuccinimide and the following indicated organic acids in HCl saturated tetrahydrofuran one obtains the following compounds with acetic acid:

7α-bromo-6β,17a-diacetoxy-1α,2α-methylene-D-homo-4-pregnen-3,20-dione, UV: $\epsilon_{228} = 13,400$, 7α-chloro-6β,17a-diacetoxy-1α,2α-methylene-D-homo-4-pregnen-3,20-dione, UV: $\epsilon_{230} = 12,600$ with formic acid:

7α-bromo-6β-formyloxy-17a-acetoxy-1α2α-methylene-D-homo-4-pregnen-3,20-dione, UV: $\epsilon_{230} = 12,700$.

7α-chloro-6β-formyloxy-17a-acetoxy-1α2α-methylene-D-homo-4-pregnen-3,20-dione, UV: $\epsilon_{230}$ = 12,500.

The preparation of the aforesaid $\Delta^6$-D-homo-steroids can be carried out by analogy to known methods, using as an example the preparation of 17a-acetoxy-1α,2α-methylene-D-homo-4,6-pregnadien-3,20-dione described below:

50.0 g. of 3β-hydroxy-D-homo-5,17-pregnadien-20-one was dissolved in 500 ml. of methylene chloride, 750 ml. of ethanol and 3.5 l. of methanol and then was treated at 35°C. with 40 ml. of 4N sodium hydroxide solution and 50 ml. of 30% hydrogen peroxide. After a reaction time of 4 days at 35°C. during which time there were twice daily additions of 40 ml. of 30% hydrogen peroxide portions, the reaction solution was concentrated in vacuo at 35°C., the residue diluted with methylene chloride and washed free of hydrogen peroxide with water. After drying over sodium sulfate, the solution was evaporated to dryness in vacuo and the residue was stirred for 30 minutes at 60°C. in 200 ml. of pyridine and 100 ml. of acetic anhydride. Upon addition to ice-water crystals precipitated out. They were washed well with water, taken up in methylene chloride and dried. After chromatography on silica gel, the product was crystallized from diisopropylether to give 21.3 g. of 3β-acetoxy-17α,17a-epoxy-D-homo-5-pregnen-20-one melting at 161°–163°C.

14.0 g. of 3β-acetoxy-17α,17a-epoxy-D-homo-5-pregnen-20-one was treated in 140 ml. of acetic acid with 42 g. of lithium bromide and then stirred for two days at room temperature. The solution was stirred into ice water, the crystals filtered off, washed well with water, taken up in methylene chloride and dried. After concentration there was obtained 17.4 g. of crude 17β-bromo-17a-hydroxy-3β-acetoxy-D-homo-5-pregnen-20-one.

The above crude compound was dissolved in 174 ml. of benzene and 174 ml. of tetrahydrofuran. It was then treated under a stream of nitrogen with 17.4 ml. of tributyl tin hydride and 870 ml. of α, α'-azo-isobutyronitrile and stirred for 1.5 hours at 60°C. The solution was concentrated in vacuo, the residue treated with pentane, the crystals filtered off and recrystallized from ethyl acetate. There was thus obtained 3β-acetoxy-D-homo-5-pregnen-20-one melting at 208°–210.5°C.

A total of 7.25 g. of 17a-hydroxy-3β-acetoxy-D-homo-5-pregnen-20-one in 36 ml. of acetic acid, 11 ml. of acetic anhydride and 1.45 g. of p-toluenesulfonic acid was stirred for 18 hours at room temperature. After throwing into ice water and filtration of the resulting crystals, the product was taken up in methylene chloride, dried and concentrated. Recrystallization from methanol yielded 7.1 g. of 3β,17a-diacetoxy-D-homo-5-pregnen-20-one melting at 126°–127°C.

A total of 7.0 g. of the above diacetoxy compound was dissolved in 70 ml. of methanol and 7 ml. of water and treated with 3.5 g. of potassium carbonate for 15 minutes at reflux. After throwing into water containing a small amount of acetic acid and filtering off of the crystals, the product was taken up in methylene chloride, dried and concentrated. Recrystallization from diisopropyl ether/methylene chloride yielded 6.0 g. of 3β-hydroxy-17a-acetoxy-D-homo-5-pregnen-20-one melting at 184°–188°C.

A total of 25.4 g. of the above compound was heated to boiling to 508 ml. of toluene, 50.8 ml. of cyclohexanone and then treated with a solution of 11.6 g. of aluminum isopropylate in 100 ml. of toluene. Thereafter the reaction mixture was slowly distilled off by heating over two hours. The remaining reaction solution was diluted with benzene, washed with dilute sulfuric acid and water and then concentrated. The residue was chromatographed on silica gel and there was thus obtained 22.3 g. of crude 17a-acetoxy-D-homo-4-pregnen-3,20-dione. A sample recrystallized from diisopropyl ether/methylene chloride melted at 221.5°–223.5°C. UV: $\epsilon_{240}$ = 16,300.

A total of 1.0 g. of the above dione in 30 ml. of dioxane was treated with 2.2 g. of 2,3-dichloro-5,6-dicyclo-p-benzoquinone, thereafter for about one minute dry hydrogen chloride gas was introduced and then the mixture was stirred into saturated sodium bicarbonate solution, extracted with chloroform and concentrated to dryness in vacuo. The residue was chromatographed on silica gel and was recrystallized from the isopropyl ether/methylene chloride to give 500 mg. 17a-acetoxy-D-homo-1,4,6-pregnatrien-3,20-dione melting at 183.5°–185.5°C. UV: $\epsilon_{220}$ = 11,000; $\epsilon_{252}$ = 9940, $\epsilon_{300}$ = 10,600.

A total of 19.25 g. of trimethylsulfoxonium iodide was dissolved in 300 ml. of dimethylsulfoxide, treated with 1.375 g. of pulverized sodium hydroxide and then stirred for 45 minutes at room temperature. Into this solution there was added 5.5 g. of the above triene and stirring was continued for an additional 5 hours at room temperature. It was then stirred into ice water containing a small amount of acetic acid, the crystals were filtered off and taken up in methylene chloride, the methylene chloride was dried and then concentrated to dryness. The residue was chromatographed on silica gel. After recrystallization from ethyl acetate there was obtained 2.5 g. of 17a-acetoxy-1α,2α-methylene-D-homo-4,6-pregnadien-3,20-dione melting at 217.5°–225°C. UV: $\epsilon_{282}$ = 16,500.

EXAMPLE 1

A total of 1.0 g. of 7α-bromo-6β-hydroxy-17a-acetoxy-1α,2α-methylene-D-homo-4-pregnen-3,20-dione was dissolved in 20 ml. of ethanol and 10 ml. of acetone, treated with a solution of 1 g. of potassium carbonate in 2.5 ml. of water and then stirred for 48 hours at 25°C. Thereafter it was thrown into water, crystals filtered off, washed, dried and recrystallized from acetone/hexane. There was thus obtained 17a-acetoxy-6β,7β-epoxy-1α,2α-methylene-D-homo-4-pregnen-3,20-dione. UV $\epsilon_{240}$ = 15,600.

In analogy to the above procedure this same 6β,7β-epoxide analog can be obtained from 7α-bromo-6β,17a-diethoxy-1α,2α-methylene-D-homo-4-pregnen-3,20-dione and from 7α-bromo-6β-formyloxy-17a-acetoxy-1α,2α-methylene-D-homo-4-pregnen-3,20-dione.

EXAMPLE 2

A solution of 0.1 g. of 7α-chloro-6β-hydroxy-17a-acetoxy-1α,2α-methylene-D-pregnen-3,20-dione in 2.4 ml. of methanol was treated with 60.0 mg. of potassium carbonate in 3 ml. of water and then heated to boiling for 3 hours. Thereafter it was thrown into water, the precipitated crystals filtered off, taken up in methylene chloride, washed with water, dried and concentrated in vacuo. After chromatography on Kieselgel and recrystallization from isopropyl ether there was obtained 17a-ethoxy-6β,7β-epoxy-1α,2α-methylene-D-homo-4-pregnen-3,20-dione. UV: $\epsilon_{240} = 15,600$.

The same 6β,7β-epoxide may be prepared in analogous fashion from 7α-chloro-6β,17a-diethoxy-1α,2α-methylene-D-homo-4-pregnen-3,20-dione and from 7α-chloro-6β-formyloxy-17a-acetoxy-1α,2α-methylene-D-homo-pregnen-3,20-dione.

EXAMPLE 3

A total of 0.30 g. of 7α-bromo-6β-hydroxy-17a-acetoxy-1α,2α-methylene-D-pregnen-3,20-dione was dissolved in 6.0 ml. of ethanol, treated with a solution of 0.15 g. of potassium carbonate in 0.75 ml. of water and then heated to boiling for 24 hours. Thereafter it was thrown into water, the crystals filtered off, washed, dried and chromatographed over silicagel. There was thus obtained 17a-acetoxy-6β,7β-epoxy-1α,2α-methylene-D-homo-4-pregnen-3,20-dione. UV: $\epsilon_{240} = 15,200$.

EXAMPLE 4

A solution of 500 mg. of 7α-bromo-6β-hydroxy-17a-acetoxy-1α,2α-methylene-D-homo-4-pregnen-3,20-dione in 10 ml. of ethanol and 5 ml. of acetone was treated with 2.5 ml. of a 20% aqueous potassium carbonate solution and stirred 30 minutes at room temperature. The mixture was thrown into water, dried in vacuo and chromatographed over silica gel. There was thus obtained 17a-hydroxy-6β,7β-epoxy-1α,2α-methylene-D-homo-4-pregnen-3,20-dione. UV: $\epsilon_{240} = 14,900$.

EXAMPLE 5

A total of 1.0 g. of 7α-bromo-6β-hydroxy-17a-hexanoyloxy-1α,2α-methylene-D-homo-4-pregnen-3,20-dione was treated in the manner of Example 1. The crude product was chromatographed over silica gel. There was thus obtained 17a-hexanoyloxy-6β,7β-epoxy-1α,2α-methylene-D-homo-4-pregnen-3,20-dione as a viscous oil. UV: $\epsilon_{240} = 15,400$.

We claim:
1. A compound of the formula

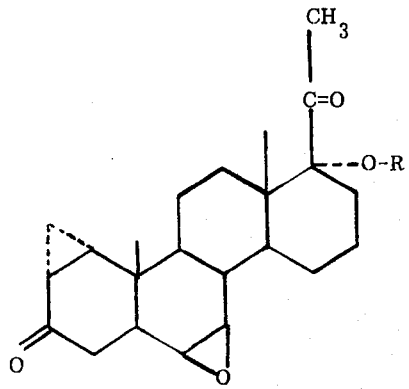

wherein R is hydrogen or a $C_{1-15}$ organic carboxylic acid radical conventionally employed in steroid chemistry as an esterifying agent for hydroxy groups.

2. The compound of claim 1 which is 17a-acetoxy-6β,7β-epoxy-1α,2α-methylene-D-homo-4-pregnen-3,20-dione.

3. The compound of claim 1 which is 17a-hexanoyloxy-6β7β-epoxy-1α,2α-methylene-D-homo-4-pregnen-3,20-dione.

4. The compound of claim 1 wherein R is hydrogen, that is 17a-hydroxy-6β,7β-epoxy-1α,2α-methylene-D-homo-4-pregnen-3,20-dione.

* * * * *